United States Patent [19]

Rusnak et al.

[11] Patent Number: 5,137,695

[45] Date of Patent: Aug. 11, 1992

[54] APPARATUS FOR THE SEQUENTIAL PERFORMANCE OF CHEMICAL PROCESSES

[75] Inventors: Miro Rusnak, LaVerne; John E. Shively; Jimmy R. Calaycay, both of Arcadia, all of Calif.

[73] Assignee: City of Hope, Duarte, Calif.

[21] Appl. No.: 582,978

[22] PCT Filed: Feb. 8, 1990

[86] PCT No.: PCT/US90/00751

§ 371 Date: Sep. 28, 1990

§ 102(e) Date: Sep. 28, 1990

[87] PCT Pub. No.: WO90/09595

PCT Pub. Date: Aug. 23, 1990

Related U.S. Application Data

[63] Continuation of Ser. No. 307,742, Feb. 8, 1989, abandoned.

[51] Int. Cl.[5] .............................................. G01N 33/68
[52] U.S. Cl. .................................... 422/116; 422/103; 422/68.1; 422/70; 436/89
[58] Field of Search ................ 422/116, 81, 101, 103, 422/67, 110, 68.1; 137/606, 804, 625.11

[56] References Cited

U.S. PATENT DOCUMENTS

| | | | |
|---|---|---|---|
| 913,516 | 2/1909 | Lake | 137/606 |
| 1,230,212 | 6/1917 | Petran et al. | 137/606 |
| 3,175,801 | 3/1965 | Taconis | 137/606 |
| 3,892,531 | 7/1975 | Gilbert | 422/116 |
| 4,252,769 | 2/1981 | Hood et al. | 436/89 |
| 4,558,845 | 12/1985 | Hunkapiller | 137/606 |
| 4,563,336 | 1/1986 | McKnight | 422/103 |
| 4,603,114 | 7/1986 | Hood et al. | 436/89 |
| 4,610,847 | 9/1986 | Hood et al. | 436/89 |
| 4,703,913 | 11/1987 | Hunkapiller | 137/606 |
| 4,704,256 | 11/1987 | Hood et al. | 422/81 |

OTHER PUBLICATIONS

Edman et al., "A Protein Sequenator" European J. Biochem. 1:80–91 (1967).
Laursen, "Solid-Phase Edman Degradation", Eur. J. Biochem. 20:89–102 (1971).
Hawke et al., "Microsequence Analysis of Peptides and Proteins, Design and Performance of a Novel Gas-Liquid-Solid Phase Instrument" Analytical Biochemistry, 147:315–330 (1985).
Shively, "Methods of Protein Microcharacterization", Huma Press, Clifton, N.J. (1986).
Fisher Scientific Catalog, 1988, p. 541.
Hewick et al., "A Gas-Liquid Solid Phase Peptide and Protein Sequenator," J. Biol. Chem. 256(15):7990–7997 (1981).

Primary Examiner—Robert J. Warden
Assistant Examiner—T. A. Trembley
Attorney, Agent, or Firm—Edward S. Irons

[57] ABSTRACT

A compact apparatus having a gravity assisted, substantially linear, vertical fluid flow path through vertically aligned elements for the N-terminal and C-terminal sequencing of proteins and peptides is disclosed.

2 Claims, 12 Drawing Sheets

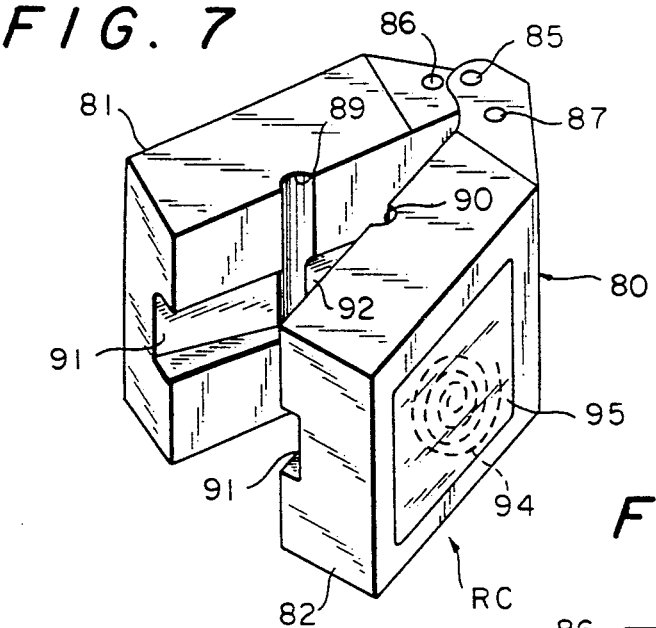
FIG. 7
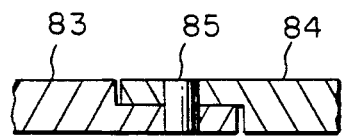
FIG. 10
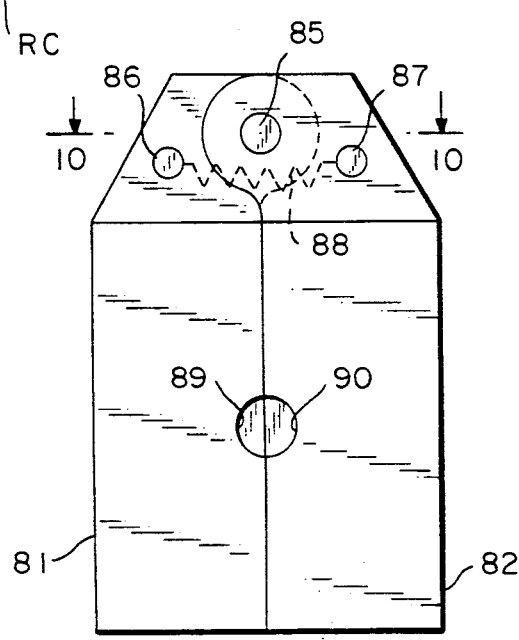
FIG. 9
FIG. 8

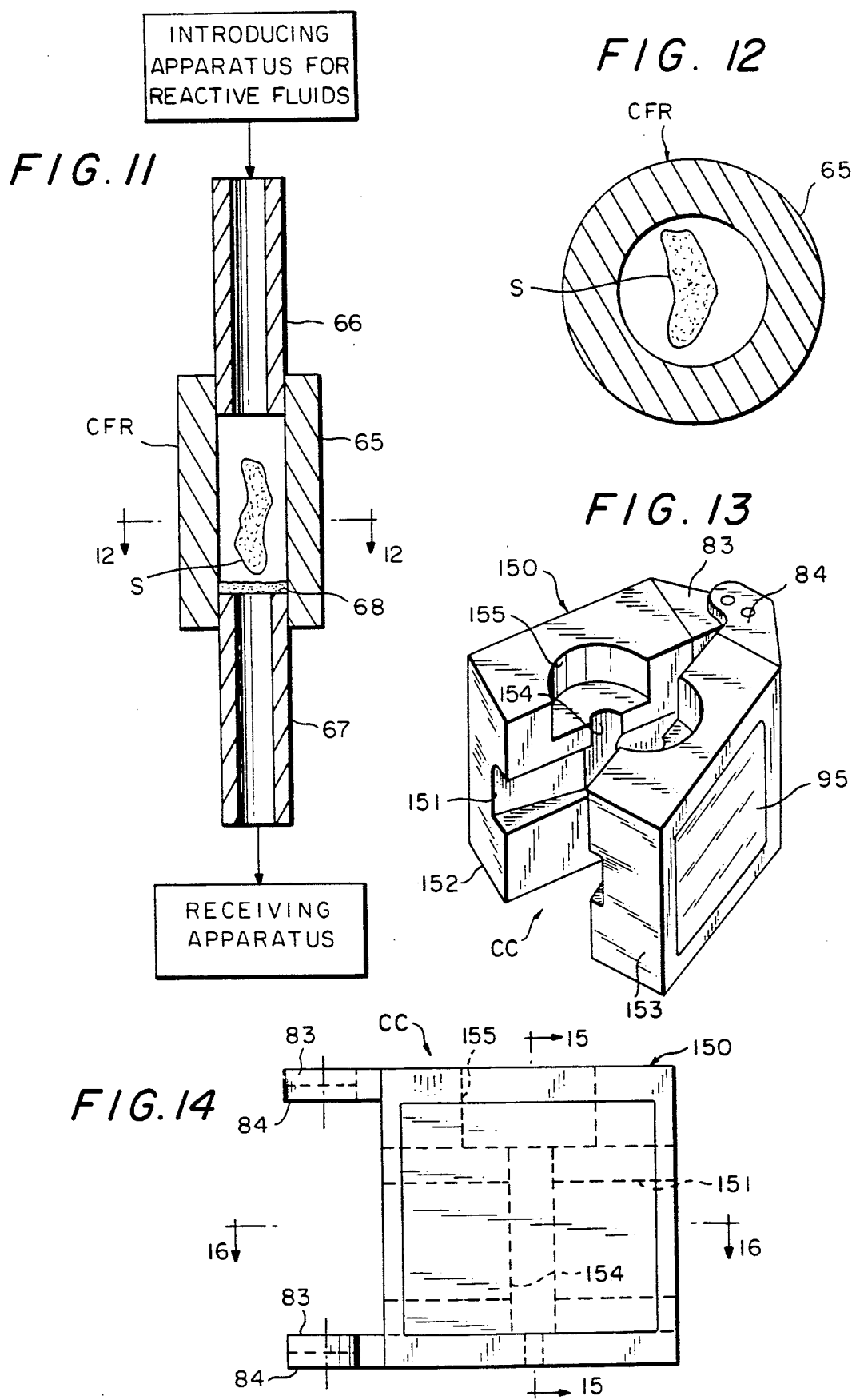

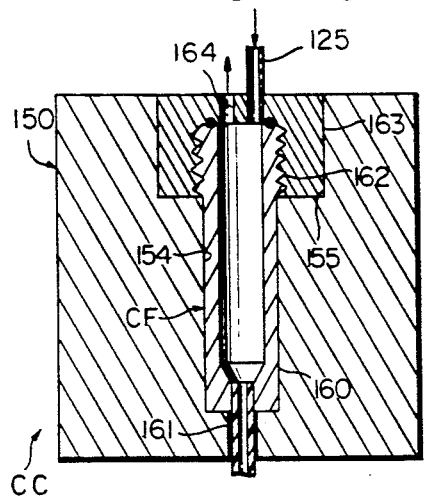
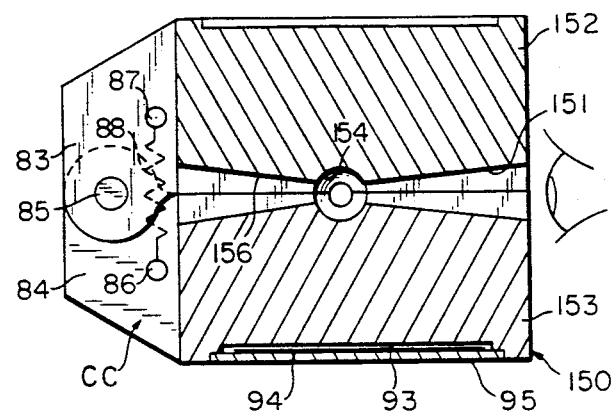
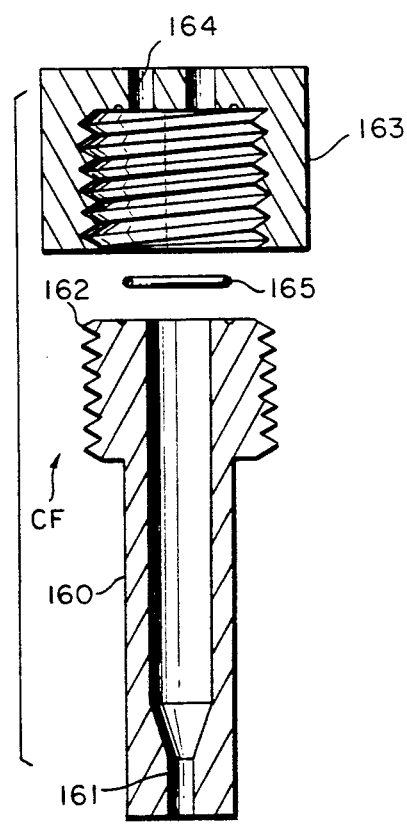
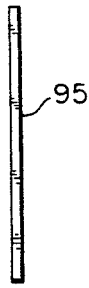
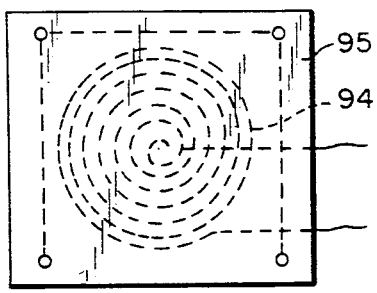

APPARATUS FOR THE SEQUENTIAL PERFORMANCE OF CHEMICAL PROCESSES

This application is a continuation of U.S. Ser. No. 307,742 filed Feb. 8, 1989 now abandoned.

FIELD OF THE INVENTION

This invention relates generally to apparatus and for the performance of sequential chemical processes. More particularly, the invention relates to apparatus for the N-terminal and C-terminal sequencing of peptides.

DESCRIPTION OF THE PRIOR ART

The linear sequence of the amino acid units in proteins and peptides is of considerable interest as an aid to understanding their biological functions and ultimately synthesizing compounds performing the same functions. Although a variety of techniques have been used to determine the linear order of amino acids, probably the most successful is known in various forms as the Edman Process. The Edman sequential degradation processes involve three stages: coupling, cleavage and conversion. In the coupling stage, phenylisothiocyanate reacts with the N-terminal β amino group of the peptide to form the phenylthiocarbamyl derivative. In the cleavage step, anhydrous acid is used to cleave the phenylthiocarbamyl derivative to form the anilinothiazolinone. After extraction of the thiazolinone, the residual peptide is ready for the next cycle of coupling and cleavage reactions. Aqueous acid is used to convert the thiazolinone to the phenylthiohydantoin which may be analyzed in an appropriate manner, such as by chromatography.

Practical automated N-terminal peptide sequencing dates from the 1967 introduction of the liquid phase spinning cup sequencer in which the reactions proceed in a thin liquid film formed on the inside wall of rotating reaction cells. See Edman, P., and Begg, G., A Protein Sequenator, *European Journal of Biochemistry*, 1:80–91 (1967). A focal problem associated with the spinning cup sequencer is sample loss, particularly of short peptides. An alternative solid phase degradation method entails passing reagents and solvents in an appropriate program through a column packed with porous material such as a macroporous polystyrene matrix or preferably porous glass beads to which a peptide is attached covalently or by adsorption. In another, known type of automatic sequencer the peptide to be degraded is covalently linked to a gel-type of solid phase support contained within a tubular reaction chamber. Both the reaction chamber and the tubing by which it is connected to the sequencer may be formed from polytetrafluoroethylene, e.g., "Teflon". See Laursen, R. A., A Solid-Phase Peptide Sequenator, *European Journal of Biochemistry*, 20:89–102 (1971) and Shively, "Methods of Protein Mischaracterization" Humana Press, Clifton, N.J. (1986), Chapter 9.

A sequencer that employs gas phase reagents instead of liquid phase reagents at critical points in the Edman degradation was proposed in 1981. See Hewick, R. M., Hunkapillar, M. W., Hood, L. E., Dreyer, W. J., A Gas-Liquid Solid Phase Peptide and Protein Sequenator, *The Journal of Biological Chemistry*, 256:7990–7997 (1981), U.S. Pat. No. 4,603,114 and Shively, supra, Chapter 8, Section 314, p. 229. This device includes a two-part glass cartridge assembly which houses a miniature continuous flow glass reaction chamber in which the peptide sample is presented as a dispersion in a thin film of a polymeric quaternary ammonium salt, such as polybrene, supported on a porous glass fiber disk. Means are provided for disconnecting the cartridge from its mounting base each time the sample is loaded.

A modification of the Hewick, et al. sequencer is described by Hawke, Harris and Shively in *Analytical Biochemistry*, 147:315–330 (1985), and Shively, supra, Chapter 7, page 210, et. seq. This modification replaces the glass reactor cartridge assembly of Hewick, et al. with an all Teflon cartridge of similar design, thus providing an all Teflon delivery and reaction system. The sample is presented within the reaction chamber on a trimethylsilyated glass fiber disk. Hawke, et al., noting that Teflon is "self-sealing", report lower background levels and increased yields deemed to be consequent from a better seal achieved in the all Teflon design as compared to the seal observed with the Hewick glass cartridge. See Shively, supra, at p. 217.

A multipurpose sequencer constructed in units which are interchangeable for easy conversion to a spinning cup, column, or cartridge operational mode has been described. A polyfluorochloro (Kel-F) micro column unit filled with peptide bound glass support objects which has Teflon tubing inlet and outlet lines for attachment to a sequencer is provided. See Shively, supra, page 249, et. seq.

Carboxyl-terminal (C-terminal) sequencing methodologies also involve coupling, cleavage and conversion stages. Known processes are enzymatic physical or chemical. The enzymatic approach is basically a time-course carboxypeptidase procedure. It is limited by differential hydrolysis rates of the involved peptide bonds and by potential unaccessibility of the COOH carboxyl terminus in proteins. The results may include the correct amino acids but in the wrong order and may not extend to more than three to five amino acids.

Physical approaches include mass spectrometry and nuclear magnetic resonance (NMR) and are most suitable for small peptides. Fast atom bombardment—Mass Spectrometry (FAB/MS) sensitivity for determining an entire peptide sequence is in the range of 1–10 nmol and is limited to expensive multisector instruments. Micromolar samples are required for NMR analysis.

Four chemical methods of some interest are known. In 1978 Parkam and Loudon reported a method in which the carboxyamido peptide derivative is treated with bis(1,1 trifluoroacetoxy)- iodobenzene to yield a derivative of the amino acid. Free COOH groups were treated with bis-p-nitrophenylphosphoryl azide to generate the carboxyamido derivative through a Curtius rearrangement. See, Parham, M. E. and Loudon G. M. *Biochem. Biophys. Res. Commun.* 80:1–7 (1978).

Loudon and coworkers presented another version of the method which entailed reaction of the COOH terminus with pivaloylhydroxyl amine in the presence of carbodimide to effect a Lossen rearrangement. This method failed to degrade aspartic and glutamine residues. See, Miller, M. J. and Loudon, G. M., *J. Am. Chem. Soc.* 97:5296 (1975); Miller, M. J., et al., *J. Org. Chem.* 42:1750 (1977).

The method reported by Stark releases the COOH-terminal amino acid as a thiohydantoin. See, Stark, G. R. *Biochemistry* 8:4735 (1968); Stark, G. R. in "Methods in Enzymology", Vol. 25, p. 369, Academic Press, New York, New York (1972). It entails activation of the COOH group with acetic anhydride, followed by reaction with ammonium thiocyanate and cleavage by acid or base hydrolysis to release the thiohydantoin from the peptide chain.

Hawke reported a modification of the Stark chemistry in which trimethylsilylisothiocyanate is utilized as the coupling reagent. See, Hawke, et al. *Analytical Biochemistry* 166:298-307 (1987).

Application Ser. No. 271,328, filed Nov. 15, 1988, now U.S. Pat. No. 4,935,494 issued Jun. 19, 1990, incorporated herein by reference, describes alternative chemistry for C-terminal peptide and protein sequencing.

Application Ser. No. 174,956 filed Mar. 28, 1988, now U.S. Pat. No. 5,061,635 issued Oct. 29, 1991, incorporated herein by reference, describes a continuous flow reactor (CFR) for use in the cleavage phase of a sequencer which is inexpensive and substantially free of unswept volumes thus minimizing the accumulation of by-products and reagents. The CFR is formed from chemically inert synthetic resin tubing. A reaction chamber comprising a section of such tubing of relatively large internal diameter is provided with interference fitted inlet and outlet tubes of appropriate dimension. In a preferred embodiment of the invention, the reactor is formed from Teflon tubing. It may be packed with discrete articles, e.g., porous glass beads, or a porous synthetic resin such as polystyrene coated with the protein or peptide to be sequenced. When such packings are used, a porous support member, preferably of Teflon, may be provided. Pursuant to another embodiment of the invention, the sample may be borne by a hydrophobic membrane such as polyvinyl difluoride (PVDF) to which proteins adhere. Optionally the packings or the hydrophobic membrane may be coated with a polymeric quaternary ammonium salt such as 1,5 dimethyl-1,5-diazaundecamethylene, polymethobromide or poly (N,N-dimethyl-3,5-dimethylene piperidinium chloride. One such product is available under the trademark Polybrene from Aldrich Chemical Company.

Extreme difficulty in the procurement of macroscopic quantities of biological materials is frequently encountered. Hence degradation of available peptide samples may yield only minute quantities of amino acids. Conventional sequencers yield amino acid sample volumes of a few microliters whereas much smaller volumes are required for effective microanalysis by capillary electrophoresis or comparable techniques. See, e.g., Cheng, et al., Subattomole Amino Acid Analysis by Capillary Zone Electrophoresis and Laser-Induced Fluorescence, *Science* 242:562-564 (1988).

Accordingly, in one embodiment this invention provides a miniaturized sequencer which accommodates the volume requirements of electrophoresis separation.

SUMMARY OF THE INVENTION

Pursuant to this invention, peptide N-terminal or C-terminal sequencing is efficiently accomplished in a compact apparatus of unique design. A substantially zero dead volume sequencer is provided in which a cartridge reactor or continuous flow reactor (CFR) as described, for example, in Shively application Ser. No. 174,956, now U.S. Pat. No. 5,061,635 issued Oct. 29, 1991, is preferably utilized. One embodiment of the invention comprises a miniaturized sequencer which accommodates sample volumes appropriate for amino acid analysis by capillary zone electrophoresis. The limited volumes required facilitate the use of costly high purity reagents.

BRIEF DESCRIPTION OF THE DRAWINGS

The foregoing, as well as other objects and advantages of the invention, will become apparent from the following detailed description when considered with the accompanying drawings, in which like reference characters designate like parts throughout the several views, and wherein:

FIG. 7 is a top perspective view of the hinged heater block for the reaction chamber and continuous flow reactor contained therein showing the heater block in a partially open position.

FIG. 8 is a horizontal sectional view of the heater block of FIG. 7, shown in fully opened position.

FIG. 9 is a top plan view of the heater block of FIG. 7, shown in closed position.

FIG. 10 is an enlarged sectional view taken along line 10—10 in FIG. 8.

FIG. 11 is an enlarged vertical sectional view of a reaction chamber which may be used to hold the sample in the heater block of FIGS. 1-7.

FIG. 12 is a transverse sectional view taken along line 12—12 of FIG. 11.

FIG. 13 is a top perspective view of the heater block for the conversion flask, shown in partially open position.

FIG. 14 is a side view of the heater block of FIG. 13.

FIG. 15 is a vertical sectional view taken along line 15—15 in FIG. 14.

FIG. 16 is a horizontal sectional view taken along line 16—16 in FIG. 14.

FIG. 17 is a side view in elevation of the heating element cover used in the heater block of the invention, showing one form of heating element in dotted lines.

FIG. 18 is an end edge view of the heating element cover of FIG. 17.

FIG. 19 is an enlarged, exploded view in section of the conversion flask used in the apparatus of FIG. 1.

DETAILED DESCRIPTION OF THE PREFERRED EMBODIMENTS

Figure 1:
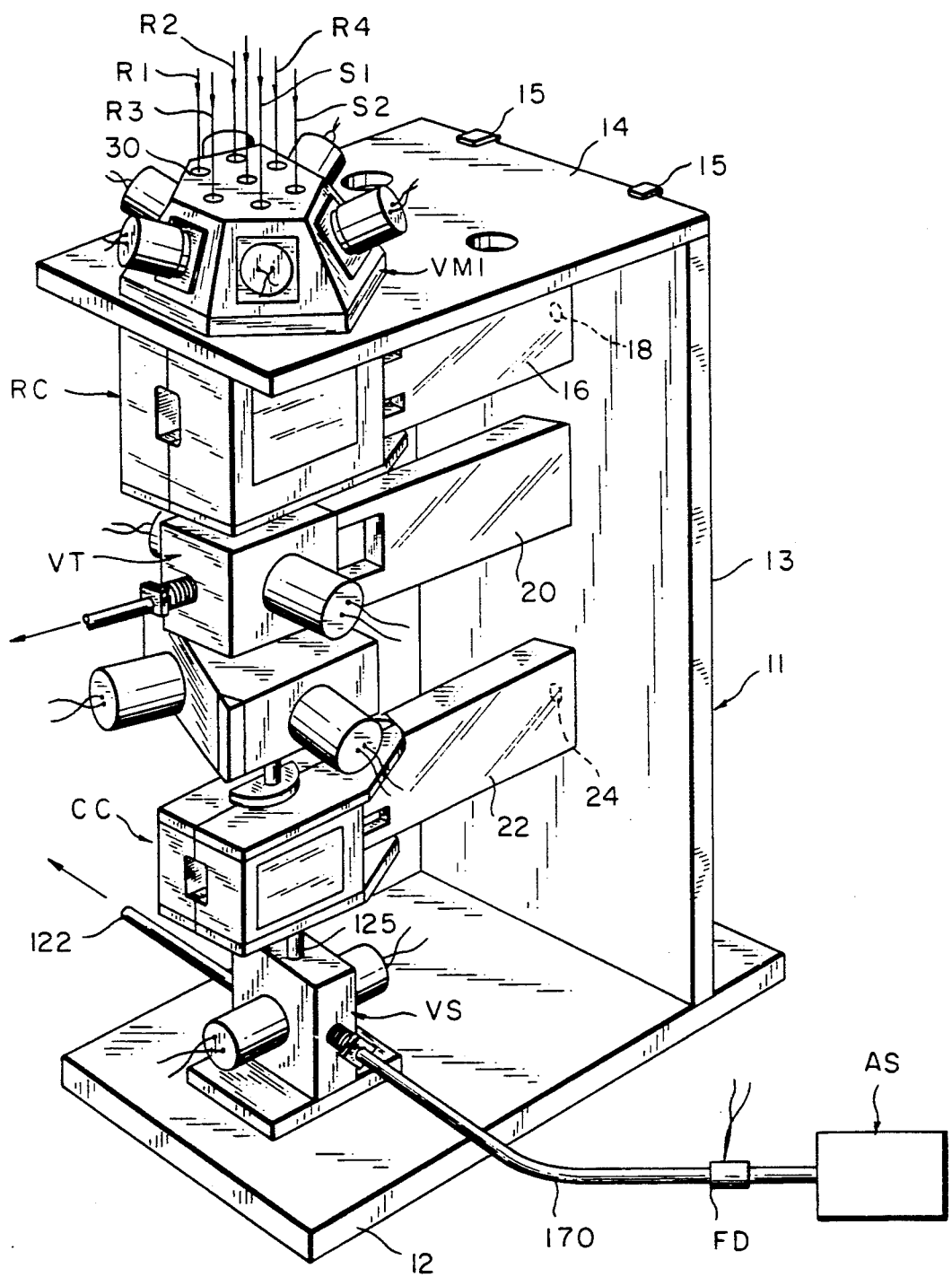
FIG. 1 is a top perspective view of one form of the apparatus according to the invention.
Figure 2:
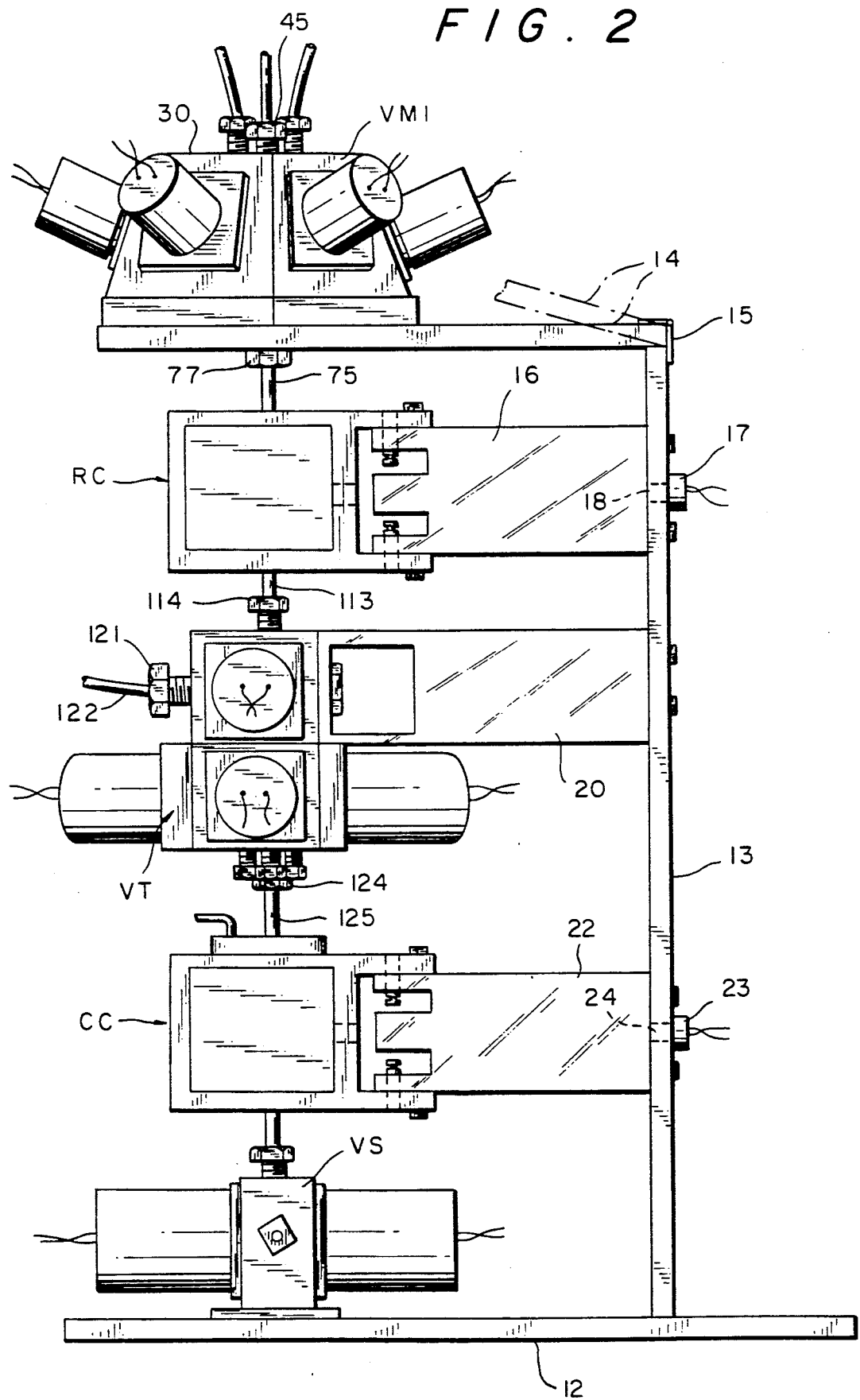
FIG. 2 is a side view in elevation of the apparatus of FIG. 1.
Figure 3:
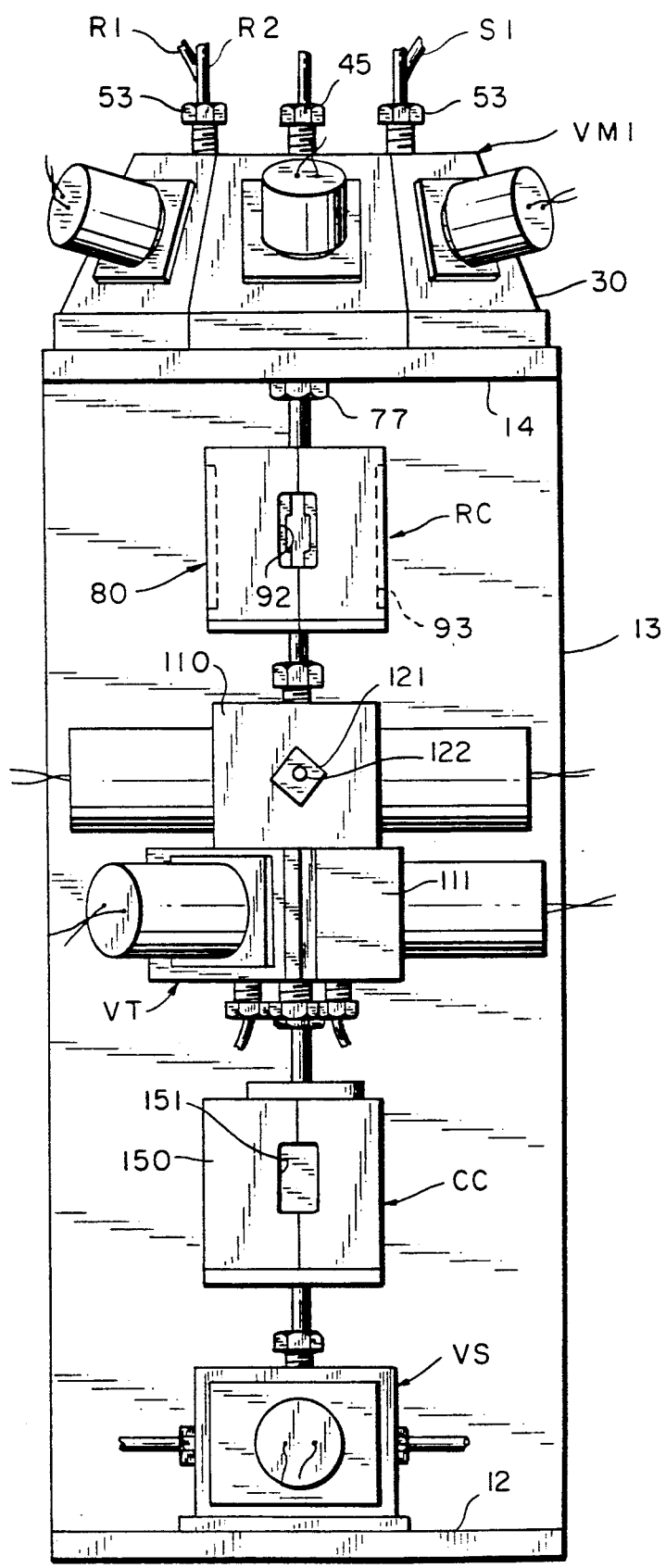
FIG. 3 is a front view in elevation of the apparatus of FIG. 1.

FIGS. 1–31 generally depict an apparatus for the performance of sequential chemical processes such as the N-terminal or C-terminal sequential degradation of peptides. As specifically illustrated, the apparatus comprises a heated coupling and reaction chamber (RC) to accommodate a reaction cartridge such as a CFR containing a peptide sample S for sequential reaction with a plurality of reagents R1, R2, and R3, and solvents S1 and S2. The actual number of reagents and solvents utilized will be determined by the chemistry selected for a particular sequencing reaction.

A multi-inlet valve VMI controls flow of the reagents and solvents to the reaction chamber, and a transfer valve VT controls flow of fluids from the reaction chamber either to waste or to a conversion flask CF confined within a heated conversion chamber CC. The conversion products are then conveyed through a selector valve VS and a fluid detection means FD to an analytical system such as a high performance liquid chromatography (HPLC) or capillary electrophoresis (CE) system.

The multi-inlet valve, reaction chamber, transfer valve, conversion chamber and selector valve are all supported on a frame 11 comprising a horizontal base 2, upright support 13 and horizontal cover 14 secured at one end with hinges 15 to the upper end of the support 13 and extending outwardly in parallel, spaced relationship over the base 12. As seen best in FIGS. 1, 2 and 3, the multi-inlet valve (VMI) is secured on top of the cover 14. The reaction chamber RC containing the CFR is secured to a light-transmitting arm 16 attached at one end to the support 13 in spaced relation below the cover 14. The reaction chamber is held in closely spaced, aligned relationship with the outlet from the multi-inlet valve. A light source 17 is mounted behind the support 13 in alignment with an opening 18 for the transmission of light through the arm to the reaction chamber.

The transfer valve VT is similarly supported on the end of a mounting arm 20 attached at one end to the support 13 in spaced relation below the reaction chamber support arm 16. The transfer valve is held in alignment with the outlet 113 (FIG. 2) from the reaction chamber.

A conversion chamber CC for a conversion flask CF is supported on one end of a second light-transmitting arm 22, attached at its other end to the support 13 in spaced relation below the transfer valve support arm 20. A light source 23 is mounted behind the support 13 in alignment with an opening 24 for the transmission of light through the arm 22 to the conversion flask.

The selector valve VS is supported above the base 12 in spaced alignment with an outlet from the conversion flask to control the flow of fluids from the conversion flask to waste or to an analytical system. A fluid detection means FD is positioned on the conduit between the selector valve and the analytical system.

The Multi-Inlet Valve

Figure 4:
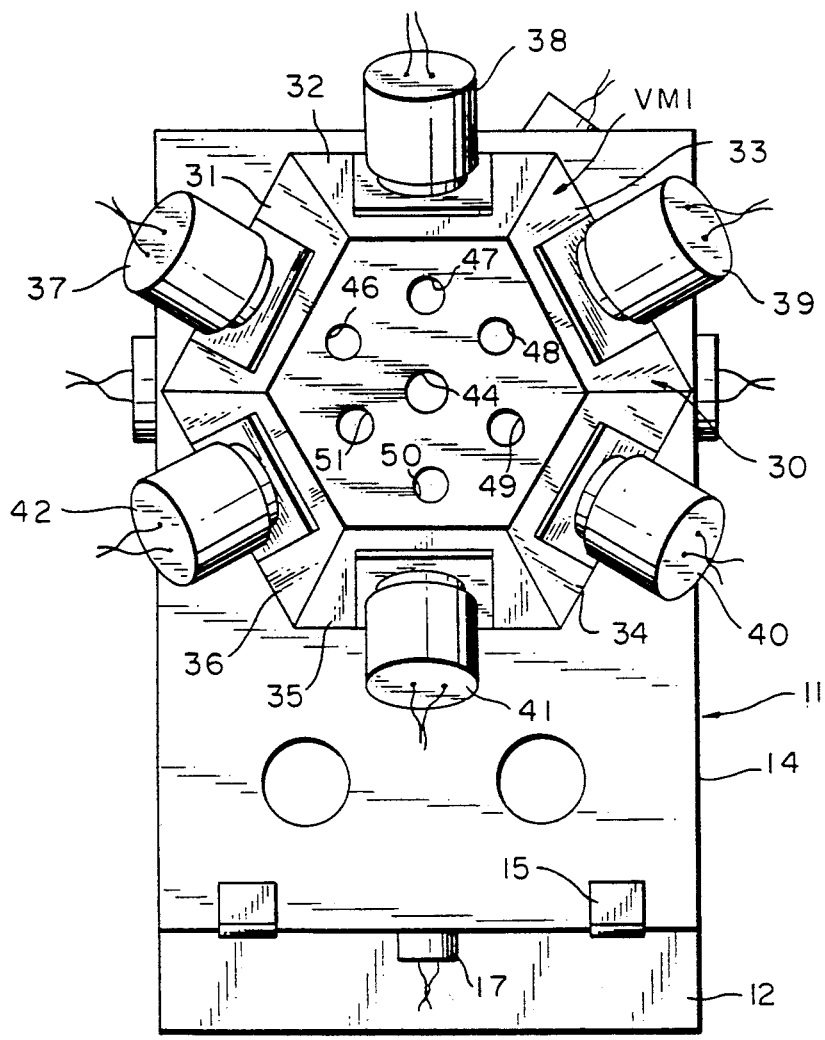
FIG. 4 is a top plan view of the apparatus of FIG. 1.
Figure 5:
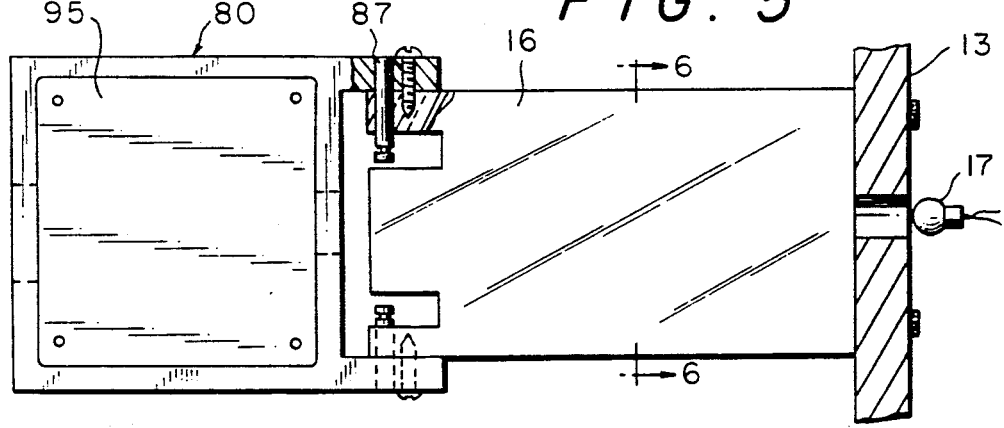
FIG. 5 is an enlarged side view in elevation of the mounting arm and hinged heater block and heating element for the continuous flow reactor (CFR) used in the apparatus of FIG. 1.
Figure 6:
FIG. 6 is a horizontal sectional view of the arm of FIG. 5.
Figure 20:
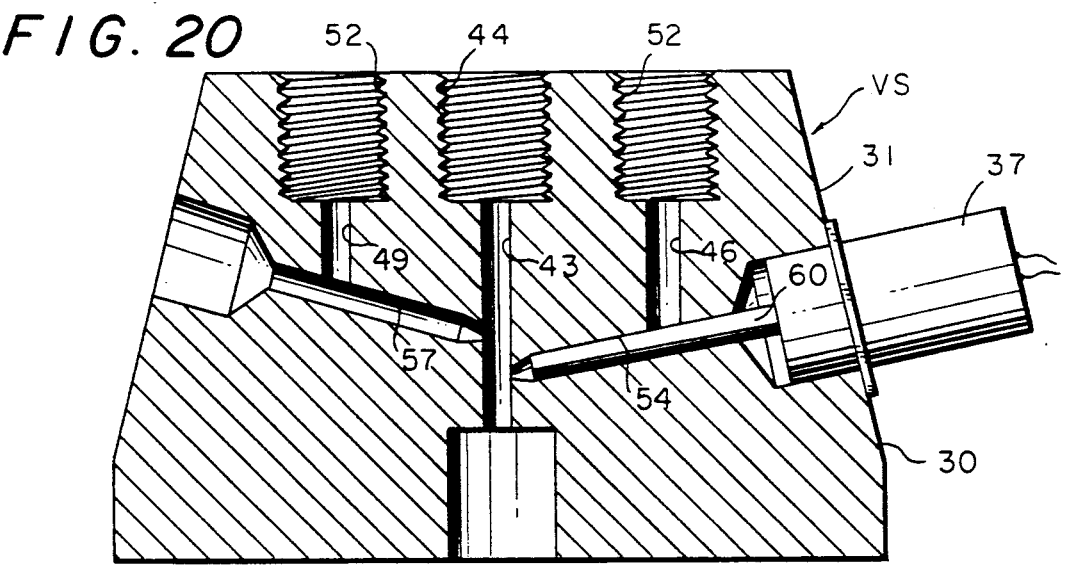
FIG. 20 is an enlarged vertical sectional view of the multi-inlet valve used in the apparatus of FIG. 1.
Figure 21:
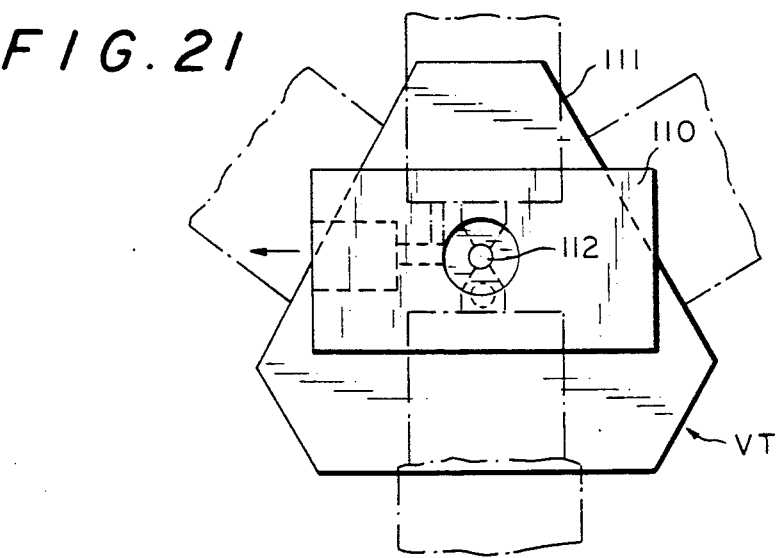
FIG. 21 is a top plan view of the transfer valve used in the apparatus of FIG. 1, with portions of the solenoids shown in dot-and-dash lines.
Figure 22:
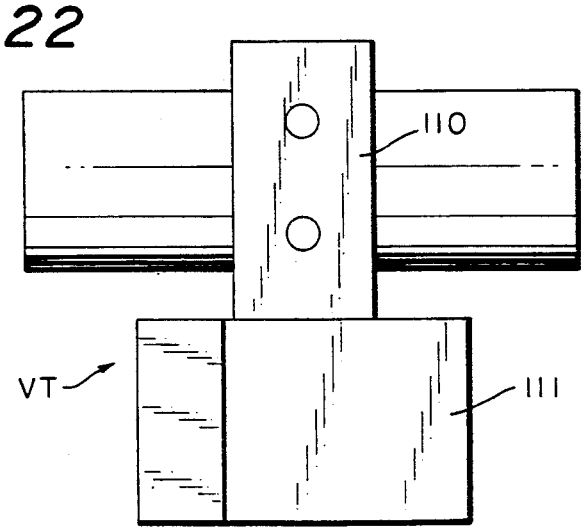
FIG. 22 is an edge view in elevation of the transfer valve.
Figure 23:
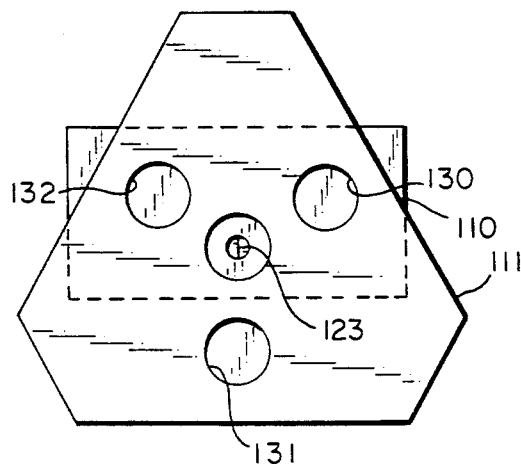
FIG. 23 is a bottom view of the transfer valve, with solenoids shown removed.
Figure 24:
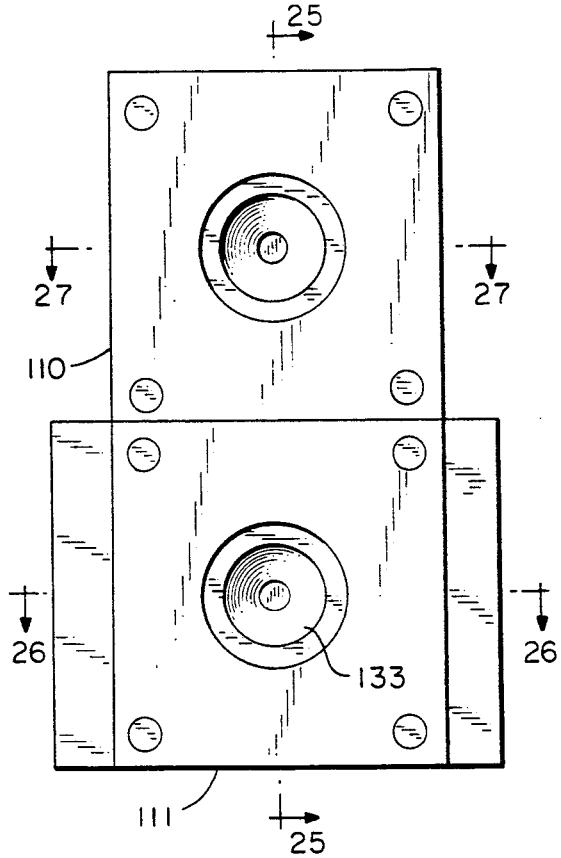
FIG. 24 is a side view in elevation of the transfer valve, with solenoids removed.
Figure 25:
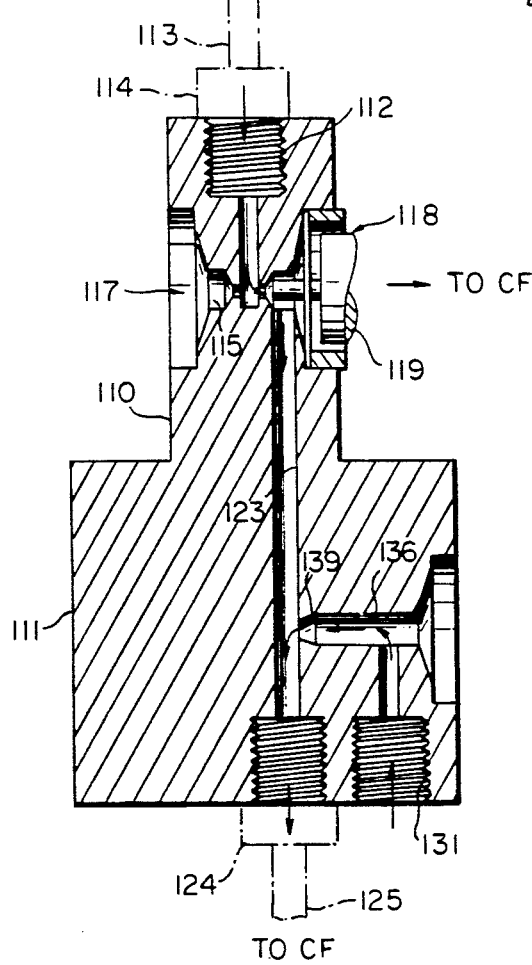
FIG. 25 is a vertical sectional view taken along line 25—25 in FIG. 24.
Figure 26:
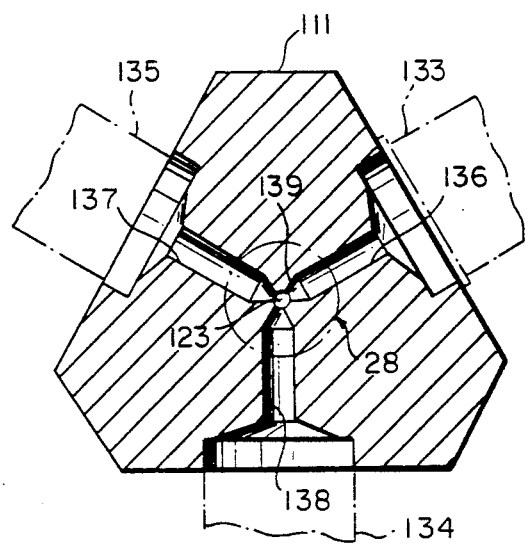
FIG. 26 is a horizontal sectional view taken along line 26—26 in FIG. 24.
Figure 27:
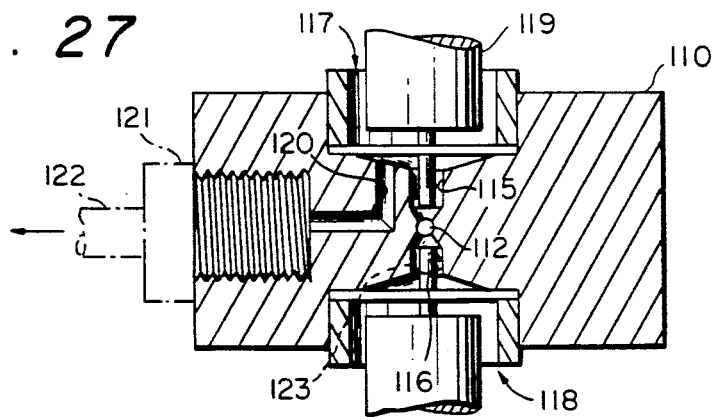
FIG. 27 is a horizontal sectional view taken along line 27—27 in FIG. 24.
Figure 28:
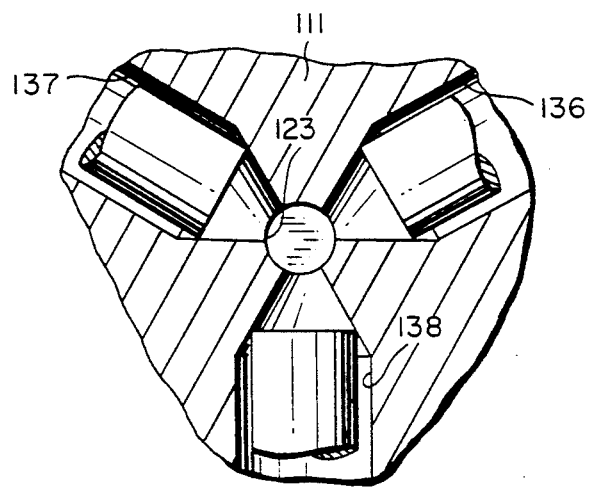
FIG. 28 is an enlargement of the area enclosed within the circle in FIG. 26.
Figure 29:
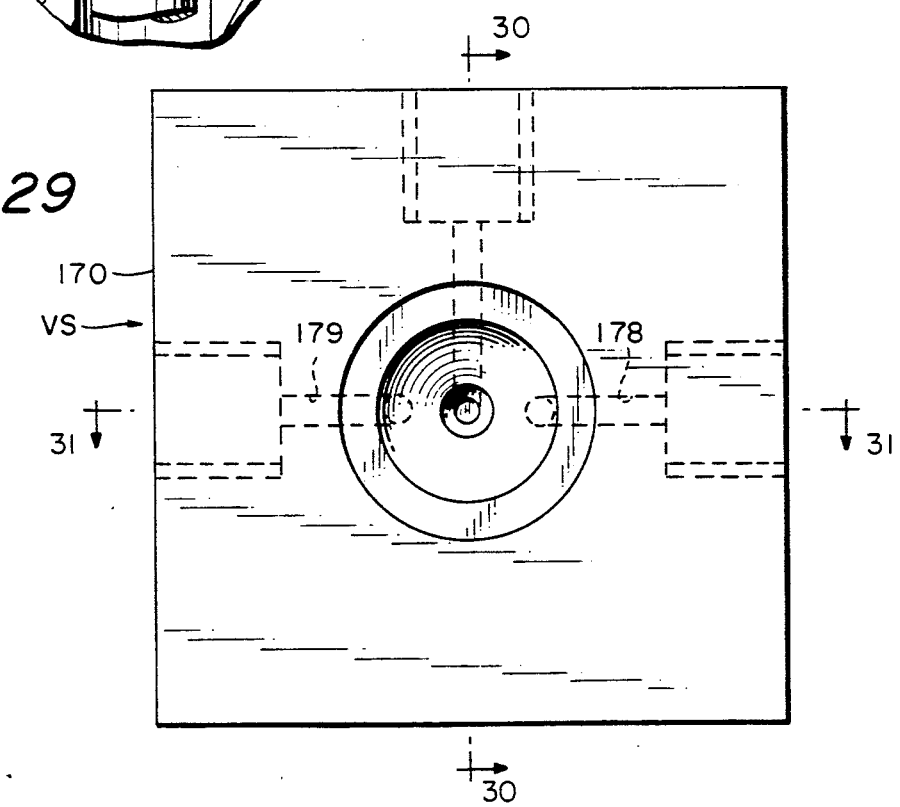
FIG. 29 is a side view of the selector valve used in the apparatus of FIG. 1.
Figure 30:
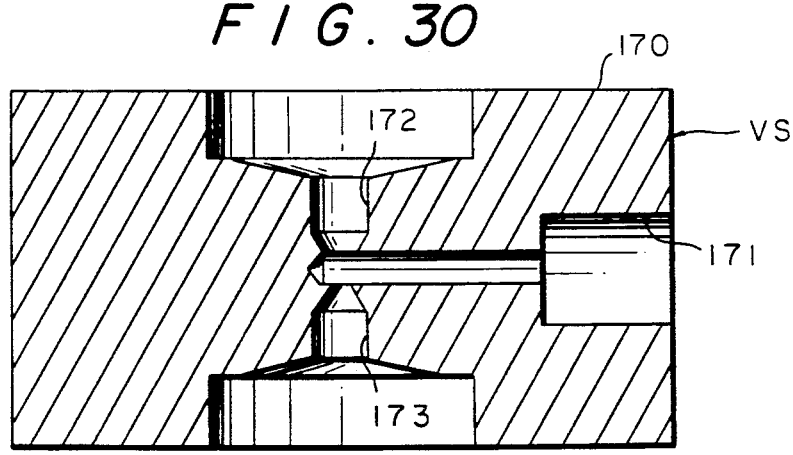
FIG. 30 is a vertical sectional view taken along line 30—30 in FIG. 29.
Figure 31:
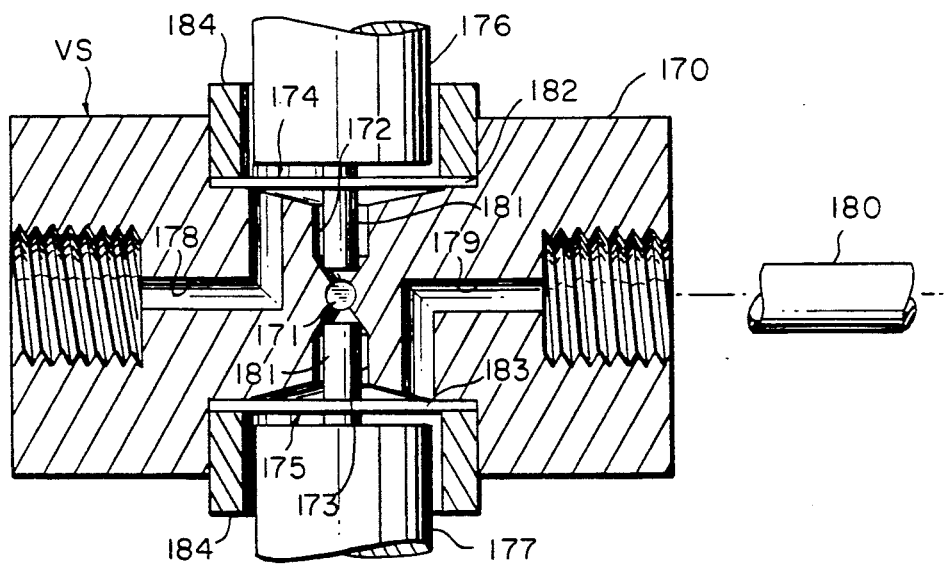
FIG. 31 is a horizontal sectional view taken along line 31—31 in FIG. 29.

As best seen in FIG. 4, the multi-inlet valve VMI comprises a compact multiport body 30 made of a material inert to the chemicals employed, and in the particular embodiment shown, has six sides 31–36, to which are fixed solenoid valve members 37–42, respectively. As seen best in FIGS. 4 and 20, a single passage 43 may extend axially downwardly through the center of the valve body, for communication at its upper end with an internally threaded enlargement 44 for attachment of a fitting 45 (FIGS. 2 and 3) leading to a source (see FIG. 33) of pressurized inert gas, such as argon. A plurality of passages 46–51 extend axially in the body in spaced relationship around the central passage, and each is controlled by one of the solenoids 37–42. Each passage 46–51 communicates at its upper end with an internally threaded enlargement 52 for attachment of a fitting 53 (FIGS. 2 and 3) leading to pressurized sources (FIG. 33) of the various reagents, R1, R2, and R3 and solvents S1, S2 and S3. At their lower ends, the passages 46–51 are in intersecting communication with downwardly inclined ports 54–59, which terminate at their lower ends in the axial central passage 43. Elongate valving pins 60 are operated by the solenoids to selectively interrupt or enable flow through the respective ports 54–59, into the central passage 43 and thence into the continuous flow reactor CFR contained in the reaction chamber RC. As seen in FIG. 20, the points of intersection of the ports 54–59 with the central passage 43 are vertically spaced or staggered in alternation with respect to one another, to provide a more compact structure. Further, the downwardly sloping orientation of the ports facilitates the use of gravity flow of the reagents and solvents.

A reaction chamber useful in the invention is shown in FIG. 1 where it is generally designated by reference character RC. As specifically illustrated in FIGS. 11 and 12, the reaction chamber encloses a CFR comprising reaction tube 65 and interference fitted supply and drain tubes 66 and 67. Each of the tubes 65, 66 and 67 is formed from a self-lubricating fluorocarbon such as a polytetrafluoroethylene.

Each of the tubes 66 and 67 may be of substantially the same size, and the reaction tube 65 may be larger than the tubes 66 and 67. For example, the tubes 66 and 67 may have an outer diameter of approximately one-sixteenth (1/16 or 0.0625) inch. The reaction tube 65 may have an inner diameter also of approximately one-sixteenth (1/16 or 0.0625) inch and an outer diameter of approximately one-eighth ⅛ or 0.125) inch. The inner diameter of the reaction tube 65 is slightly undersized relative to the outer diameters of the tubes 66 and 67. With these size relationships, leak proof joints are provided between the tubes 66 and 67 by interference or press fitting.

Alternatively, the tube 67 may be larger and so dimensioned as to provide a press fit on the outside instead of the inside of the reaction tube 65. A reaction zone free of unswept volumes is provided in this manner.

A porous support member 68, such as a disk, may be tightly fitted inside the reaction tube 65. Preferably, the support member 68 is positioned near the location of the upper edge of the tube 67 in the embodiment shown in FIG. 11. The support member 68 has a porosity requisite to allow passage of fluids and yet retain discrete objects, such as porous glass beads or a hydrophobic membrane bearing a sample S placed into the upper portion of the reaction tube 65. Support member 68 is formed from a chemically inert synthetic resin, preferably a fluorocarbon. For example, the support member 68 may be made from polytetrafluoroethylene cut by a 14-gauge needle to provide a circular disk slightly larger than the inner diameter of the reaction tube 65. The disk can be pressed into the reaction tube 65 where it will be retained in the desired position by the resulting press fit.

The removal and replacement of cartridge reactors such as a CFR are quickly and easily accomplished by reason of the hinged structure of the reaction chamber heater block. As seen best in FIGS. 1-3, 5 and 7-10, the hinged heater block for the reaction chamber comprises a bifurcated housing 80 having hinged together halves 81 and 82 pivotally connected together via pivot arms 83 and 84, through which pivot pins 85 are extended. As seen best in FIGS. 8 and 9, spring mounting pins 86 and 87 are engaged in the pivot arms in spaced relationship to the pivot pins, and a tension spring 88 is connected between the pins so that an over-center action is obtained. That is, when the housing halves are closed as seen in FIG. 9, the spring and mounting pins are positioned between the pivot pins 85 and housing halves, so that the spring biases the housing halves together. On the other hand, when the housing halves are opened as shown in FIG. 8, the mounting pins and spring are positioned on the side of the pivot pin opposite the housing halves, whereby the spring biases the housing halves apart.

Each housing half has a mating passage 89, 90 therein, providing space for accommodating a cartridge reactor such as a CFR. Channels 91, 92 extending through the front and rear of the housing 80 intersect the passages to provide an entryway for illumination through the mounting arm 16, and to provide a viewing opening for observing the reaction chamber, respectively.

The outer face of each housing half is recessed at 93 for accommodating a suitable heater, such as an electrical resistance coil or foil member 94, and a cover plate 95 is secured over the heating element.

The Transfer Valve

The transfer valve VT, as seen best in FIGS. 21-28, is also compact and reliable in design, comprising an upper body part 110 and a lower body part 111. The mounting arm 20 is attached to the upper body part 110, which has an inlet port 112 in the upper end thereof, connected to receive fluids from the reaction chamber via tubing 113 and threaded coupling or fitting 114 engaged in the inlet 112. The inlet port 112 is branched at its inner end into a pair of oppositely directed passages 115 and 116, controlled by valves 117 and 118, respectively, operated by solenoid plungers 119. The first passage 115 communicates through the valve 117 with an outlet 120, leading to waste via a threaded fitting 121 and length of tubing 122, while the second passage 116 communicates through the valve 118 with an elongate axially extending passage 123 leading to the conversion flask CF through a threaded fitting 124 and length of tubing 125.

The lower body part 111 has two inlets 130, 131 for conveying reagents and/or solvents from sources (not shown) to the conversion flask, and a vent outlet 132 in the bottom thereof, all spaced around the outlet 123. These inlet and outlet parts are controlled by valves 133, 134 and 135, having axially movable plungers extending into passages 136, 137 and 138 for cooperation with valve seats 139 to control flow from the respective inlets to the outlet 123.

The transfer valve enables solvents and gas to be flushed through the CFR for washing, drying, etc., without disturbing any process which may be under way in the conversion flask CF, by opening the waste valve 117 and closing the valve 118.

The Conversion Flask and Chamber

As seen best in FIGS. 1-3 and 13-19, the chamber for the conversion flask CF is shaped similarly to the chamber 80 for the continuous flow reactor CFR, i.e., the conversion flask CF is releasably confined in a bifurcated heating block 150. The arm 22 and light source 23 serve the same purpose as the arm 16 and light 17, and the interior of the conversion flask can be viewed through the opening 151 in the front of the heating block 150.

The conversion flask CF is removably supported in the bifurcated heating block 150, which has opposed mating halves 152 and 153 with complementally shaped cut-outs 154 and 155 in their confronting faces for receiving the conversion flask. The faces of the heating block halves also have cut-outs 151 and 156 defining a viewing opening in the front part of the block and a light-transmitting opening in the rear part of the block, respectively. Pivot arms 83 and 84 on the heating block halves are pivotally mounted on suitable pivot means 85 on the forward end of the mounting arm, whereby the halves can be pivotally opened and closed relative to one another as described in connection with the CFR heater block. Suitable spring means, such as coil spring 88 carried on the end of the mounting arm, engages the heating block halves to maintain them either closed or open, as previously described. Further, an electric resistance heating element 94 is positioned on the outer face of each half of the heating block for heating the block and conversion flask and a cover 95 is secured thereover.

Visual inspection of the materials within the conversion flask is possible through the viewing opening defined by cut-out 151 in the front of the heating block. The viewing process is facilitated by light source 23 shining through opening 24 and focused by arm 22 through opening 151 into the conversion flask CF.

The conversion flask CF is formed by an elongate tubular body 160 having a reduced diameter opening 161 in its lower end and a radially enlarged externally threaded upper end 162, to which is adapted to be releasably secured a cap 163. A length of tubing 125 is tightly engaged at its lower end in a first port 126 in the cap, and is engaged at its upper end in a threaded fitting 124 releasably engaged in the outlet port from the transfer valve. A vent opening 164 also extends through the cap 163, and an O-ring 165 is engaged between the body and cap to effect a weld.

The Selector Valve

Flow of fluids from the conversion flask is controlled by selector valve VS, which comprises a generally rectangular valve body 170 having an inlet port 171 in the top thereof, leading to branched passages 172, 173 including diaphragms 174, 175, and plungers 176, 177. A first outlet passage 178, leads to waste, and a second outlet passage 179, leads to the analytical system, such as HPLC or CE via conduit 180. The valves, as seen best in FIG. 31, include plungers 181 extending through diaphragms 174 and 175 into sealing engagement with the tapered inner end of the respective passages. Spacers 184 are seated against the diaphragms to hold them in place.

Figure 32:
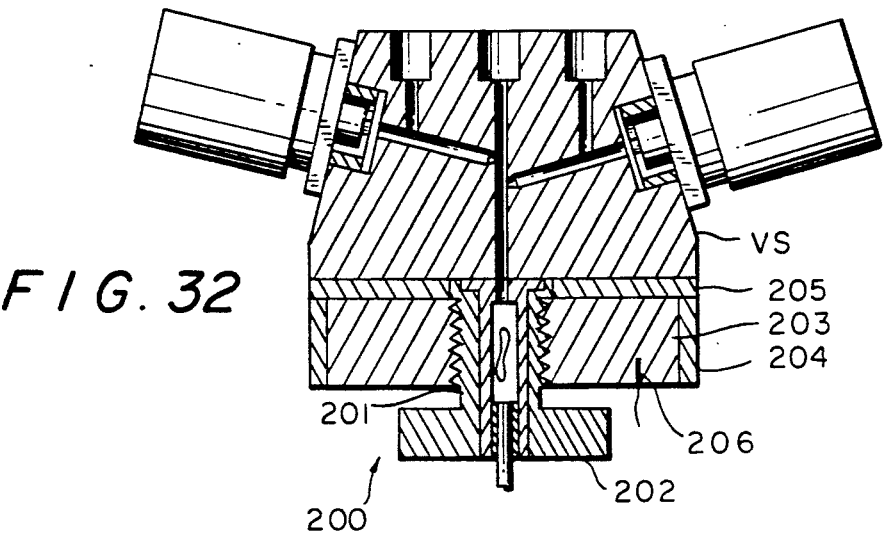
FIG. 32 is a vertical sectional view of a variation of the heater block and continuous flow reactor used in the invention.

A first variation of the invention is indicated generally at 200 in FIG. 32. In this form of the invention, the reaction chamber 201 is mounted in a threaded fitting 202 carried in a heating block 203, and is attached to the outlet from the multi-inlet valve VS. A heating element 204 at least partially surrounds the heating block, and is thermally insulated from the multi-inlet valve by an insulating spacer 205. A temperature sensor 206 may be associated with the heating block to monitor the temperature therein, if desired.

The Analytical System

Any analytical system appropriate to identify the amino acids present in the conversion reaction product may be utilized. High performance liquid chromatography (HPLC) is appropriate. The interface between the sequencer and the HPLC system may be in conventional form.

The sequencer of the invention may also appropriately be interfaced with a capillary electrophoresis system as described, for example, in the previously cited article by Cheng, et al. Interface of a CE system with the sequencer of this invention may be accomplished by positioning a packing such as an octadecylsilyl (ODS) reverse phase HPLC packing or a PVDF membrane in the conduit 170 from the selector valve for the purpose of concentrating the conversion product. The concentrated product may then be passed into a fused quartz tube friction fitted into the conduit 170 of appropriate dimensions for interface with the CE system. For example, the used quartz tube may be on the order of 0.5 millimeters in cross-section and be provided with an internal passage on the order of 40–100 $\mu$m.

After concentration, the conversion product is eluted into the fused quartz tube of the CE system and electrophoresis analysis is initiated.

The Fluid Flow Control System

Figure 33:
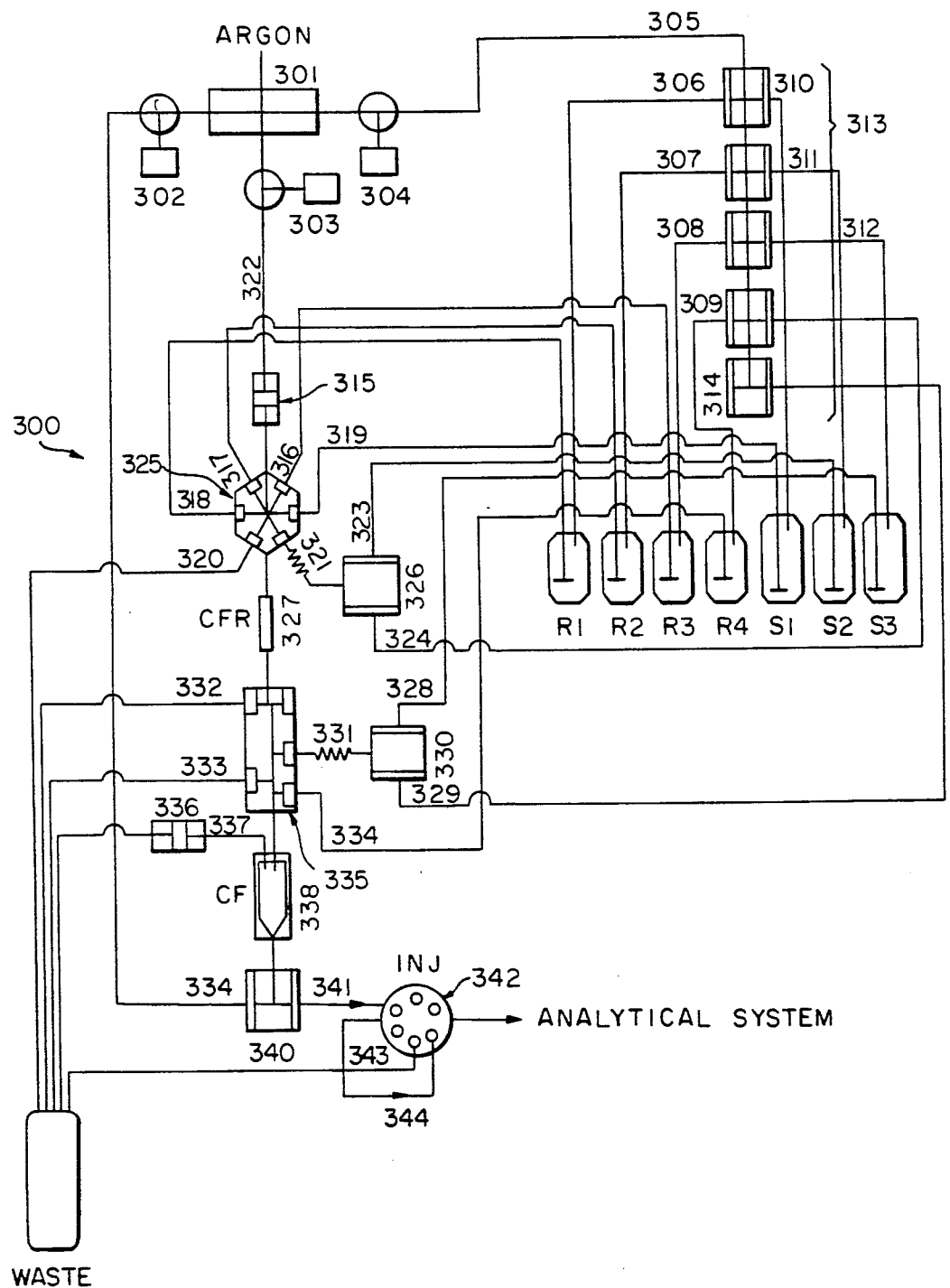
FIG. 33 is a schematic diagram of a flow control system which may be used with the device of the invention.

A flow control system for use in the invention is represented schematically at 300 in FIG. 33. As seen in this Figure, the multi-port inlet valve VMI 325 is connected at its central passage 44 via blow-out line 322, two way valve 315 and pressure gauge 303 with a four way manifold 301 and thence to a source of argon under pressure. The manifold 301 functions to distribute pressurized gas to the system as described hereinafter.

With reference to the multi-port inlet valve VMI and the system diagram in FIG. 33, port 46 (see FIG. 4) is connected via conduit 318 with reagent R1; port 47 is connected via conduit 317 with reagent R2; port 48 is connected via conduit 316 with reagent R3; port 49 is connected via conduit 319 with solvent S1; port 50 is connected via measuring loop 321 and selector valve 326 with either conduit 323, leading to solvent S2, or conduit 324 leading to manifold 313 and pressurized line 309 for reagents/solvents (it should be noted that manifold 313 has ten outlets, each controlled by a valve to provide individual pressurized gas to a reagent or solvent or as a blow-out function); and port 51 is connected via overflow line 320 to waste. As described previously, the central port 43 leads to the continuous flow reactor CFR.

The pressurized argon is connected through the manifold 301, conduit 305 and pressure gauge 304 with manifold 313 and to the various reagents/solvents. In addition, two of the outlets from the manifold 313 lead to selector valves 326 and 330, respectively. A conduit 339, serving as a bubble line for the conversion flask CF, also leads form the manifold 301, through pressure gauge 302 and to switching valve SV. Outlet 341 from the switching valve SV leads to injector 342, which leads, in turn, to the HPLC (or other analytical apparatus). An injector loop 344 is connected with the injector, and a waste conduit 343 leads to waste.

The vent from the conversion flask is connected via conduit 337 and two-way valve 336 with waste.

The transfer valve VT 335 has its vent connected through conduit 332 with waste, and also has an overflow connected through conduit 333 to waste. In connection with the latter, it should be noted that it is necessary to deliver premeasured volumes of solvents S2 and S4. The delivery of premeasured volumes of solvents S2 and S4 is accomplished by filling one of the measuring loops (321, 331) that continue into an overflow line 320, 333. When the liquid passes the overflow line, it is shut off, and the volume captured in the measuring loop is pushed into the continuous flow reactor CFR or into the conversion flask CF by pressurized gas through the blow-out line (324, 329). The vents 332, 337, respectively, for the continuous flow reactor and the conversion flask are opened for this process. Conduit 334 is connected with reagent R4.

Conduits 324 and 329 serve as blow-out lines for solvents 2 and 4, respectively.

Execution of the sequencer functions, preferably under computer control, illustrated by FIG. 4 may include:

| Delivery | |
|---|---|
| Reagent 1 | R1 bottle is pressurized (306), line 318 into multiport valve (325) is opened and CFR vent line/waste (332) of transfer valve (335) is opened, allowing flow through CFR (327). |
| Reagents 2, 3 and 4 | Identical to R1. |
| Solvent 3 | S3 bottle is pressurized (311), line 323 into selector valve (326), measuring loop (321) into multiport valve (325) and overflow line (320) are opened. When liquid passages the overflow line, overflow (320) is shut off. The liquid captured in the measuring loop (321) is then forced into the CFR (327) by pressurized gas from blow out line (324) into valve 345 of transfer valve (335) and into conversion flask (338), with CF vent line (337) opened by actuating vent valve (336). |
| Solvent 4 | S4 bottle is pressurized (312), |

| | -continued |
|---|---|
| | line 328 into selector valve (330), measuring loop (331) into transfer valve (335) and overflow line (333) are opened. When liquid passes the overflow line, overflow (333) is shut off. The liquid captured in the measuring loop (331) is then forced into the CF (338) by pressurized gas from blow-out line (329) with CF vent line (337) opened by actuating vent valve (336). |
| Blow-out | |
| CFR | Pressurized gas in blow-out line (322) is released by blow-out valve (315) into CFR, with vent line (332) opened. |
| CF into Injector/HPLC | Pressurized gas in blow out line (329) through measuring loop (331) into selector valve (335) opened. Line 341 of transfer valve (340) is opened to allow the liquid to move into the loop (344) of the HPLC injector (342). A fluid detector strategically positioned along line 343 detects the fluid and triggers a signal to switch the injector into "inject" position to direct the sample into the analytical HPLC column. |
| CF Dry | Converted fraction is dried by bubbling/introduction of a slow stream of pressurized gas through line 339 of selector valve (340) into the CF (338) with vent line (337) opened. |

The apparatus and method of this invention are broadly useful for the sequential performance of a series of chemical process steps. In particular, the invention is useful to synthesis as well as to sequence peptides.

We claim:

1. A polypeptide sequencer having a gravity assisted, substantially linear, vertical fluid flow path through vertically aligned sequence elements, said elements comprising:

(i) a delivery valve means for introducing fluids into a sequencing reaction chamber,
   said delivery valve means comprising:
      a valve body,
      a substantially linear, vertical fluid flow passage extending through said valve body from an inlet on a first surface of said valve body to an outlet on a second surface of said valve body, said outlet being connected to a sequencing reaction chamber inlet;
   (ii) a sequencing reaction chamber positioned below said delivery valve means,
      said sequencing reaction chamber comprising a substantially linear, vertical fluid flow passage extending from said sequencing reaction chamber inlet connected to said delivery valve outlet to an outlet;
   (iii) a transfer valve positioned below said reaction chamber,
      said transfer valve comprising a substantially linear, vertical fluid flow passage extending from a inlet transfer valve connected to said outlet of said fluid flow passage of said reaction chamber to an outlet; and
   (iv) a conversion flask positioned below said transfer valve,
      said conversion flask comprising a substantially linear, fluid flow passage extending from a conversion flask inlet connected to said outlet of said transfer valve to an outlet.

2. A polypeptide sequencer as defined by claim 1 further comprising:
   a selector valve positioned below said conversion flask,
      said selector valve comprising a substantially linear, vertical fluid flow passage extending from a inlet selector valve connected to said outlet of said conversion flask to means for conducting fluids to an analytical instrument.

* * * * *